(12) United States Patent
Gedon et al.

(10) Patent No.: US 6,673,954 B1
(45) Date of Patent: Jan. 6, 2004

(54) PROCESS FOR THE PREPARATION OF N-SILYLORGANOCARBAMATES

(75) Inventors: Steven C. Gedon, Williamstown, WV (US); Melinda B. Jackson, Belmont, WV (US); R. Shawn Childress, Marietta, OH (US)

(73) Assignee: General Electric Company, Pittsfield, MA (US)

( * ) Notice: Subject to any disclaimer, the term of this patent is extended or adjusted under 35 U.S.C. 154(b) by 0 days.

(21) Appl. No.: 10/368,830

(22) Filed: Feb. 19, 2003

(51) Int. Cl.[7] .................................................. C07F 7/10
(52) U.S. Cl. ...................................................... 556/420
(58) Field of Search ................................. 556/411, 420

(56) References Cited

U.S. PATENT DOCUMENTS

| | | | | |
|---|---|---|---|---|
| 5,218,133 A | * | 6/1993 | Pepe et al. |
| 5,220,047 A | * | 6/1993 | Pohl et al. |
| 5,354,880 A | * | 10/1994 | Pepe et al. |
| 5,962,721 A | * | 10/1999 | Kim et al. |

* cited by examiner

Primary Examiner—Samuel Barts

(57) ABSTRACT

A process is provided for preparing an N-silylorganocarbamate, which comprises: providing a mixture of aminoorganosilane and a catalytically effective amount of basic catalyst and; combining the mixture of aminoorganosilane and basic catalyst with an organocarbonate ester the mixture of aminoorganosilane and basic catalyst, the organocarbonate ester or both being at elevated temperature at the time of their being combined.

20 Claims, No Drawings

PROCESS FOR THE PREPARATION OF N-SILYLORGANOCARBAMATES

BACKGROUND OF THE INVENTION

1. Field of the Invention

This invention relates to a process for the preparation of an N-silylorganocarbamate from an aminoorganosilane and organocarbonate ester employing a basic catalyst.

2. Description of the Related Art

Organocarbamates have found widespread utility in such application as pesticides, herbicides, and pharmaceuticals, as well as their use in the manufacture of polyurethane foams, coupling agents and adhesion promoters. Although a number of methods currently exist for the synthesis of silylorganocarbamates, the simultaneous production in these processes of byproducts termed "heavies", as well as the generation of large quantities of hazardous wastes has proved to be problematic for their use in all but a few applications. Thus, there continues to be a need for a process that will produce an organocarbamate without the resultant production of toxic and corrosive heavies.

Typically, the reaction of an aminoorganosilane and an organocarbonate ester in the presence of an alcoholate catalyst is conducted at low temperatures, i.e., 25° to 50° C. and over long periods of time, i.e., 4 to 6 hours. The process of preparing carbamates from primary amines without using volatile byproduct producing chloroformates has also been reported. Several processes also describe the manufacture of carbamates by the oxidative carbonylation of amines with carbon monoxide (CO) in the presence of transition metal compound catalysts such as palladium (Pd), ruthenium (Ru), and manganese (Mn). They can also be formed by the reductive carbonylation of nitro compounds such as nitrobenzene with alcohols and CO in the presence of Ru, rhodium (Rh), and/or Pd compounds. It has also been reported that azides are transformed into various carbamates by using $Me_3P$ and commercially available chloroformates.

Carbamates can be formed from the direct reaction of primary amines and organocarbonates such as dimethyl carbonate (DMC). European Patent No. A 391,473, for example, describes a process for producing carbamates using reduced amounts of catalyst by first reacting a suitable amine with a cycloalkyl carbonate in the presence of a carbamation catalyst to produce a mixture of carbamates and a urea. Further reaction of the urea with the carbonate produces the corresponding carbamates, which are eventually recovered from the reaction mixture.

In German Patent No. A 3,202,690 a process for preparing aromatic urethanes is described by the reaction of aromatic amines and alkylcarbonates in the presence of an alcoholate of an alkali metal or an alkaline earth metal.

More recently, a method of preparing carbamates has been described in U.S. Pat. No. 5,962,721 to Kim et al., by reacting an amine with an alcohol and a mixed gas of $CO/O_2$ in the presence of one or more monovalent copper catalysts.

Japanese unexamined Patent Publication No. 311452/1990 discloses a process for using a base as a catalyst in which an alcoholate of a suitable alkaline metal and alkaline earth-metal is employed. However, the base prepared by this method remained in the carbamate and thus must be removed by neutralization to prevent polymerization and/or coloration during the conversion of carbamate to isocyanate.

Alternatively, silylcarbamates have also been prepared by the reaction of a suitably functionalized silylorgano halide, a metal cyanate, and monohydridic alcohol in the presence of an aprotic solvent such as N,N-dimethyl formamide. Unfortunately the necessity for large quantities of expensive solvent and yields that do not typically exceed 85% currently make this process less economically attractive.

Silyl carbamates have also been prepared through the hydrosilation of suitably functionalized allyl carbamates and allyl isocyanates with trimethoxy silane as reported in U.S. Pat. No. 5,220,047. The commercial availability of allyl carbamates and or allyl isocyanates, however, has severely limited the commercial viability of this process.

Silylorganocarbamate formation has also been obtained from the direct reaction of a suitable dialkyl carbonate and the corresponding aminoorganosilane in the presence of a basic catalyst such as sodium methylate. See, in this regard, U.S. Pat. No. 5,218,133 the contents of which are incorporated herein by reference. The tendency of dialkyl carbonates to alkylate the amino functionality at elevated temperatures, however, produces an undesired side product and reduces the yield of the silylcarbamate.

According to the process described in aforementioned U.S. Pat. No. 5,218,133 the aminoorganosilane was combined with a mixture of dimethyl carbonate and sodium methoxide at ambient temperature over 30 minutes and held at this temperature for an additional 3 hours during which a reaction producing methyl N-3-(trimethoxysilyl)propylcarbamate took place. The reaction mixture was then heated to 50°±5° for an additional hour to complete the reaction

SUMMARY OF THE INVENTION

It is an object of the present invention to provide a process for preparing an N-silylorganocarbamate, which can be used as a reactant in the further process of preparing an isocyanurate.

It is a further object of the present invention to provide the aforementioned process of preparing an N-silylorganocarbamate that can be utilized at an elevated temperature to increase the reaction rate while minimizing unwanted byproduct formation and thus resulting in greatly improved yield of the desired N-silylorganocarbamate.

In keeping with these and other objects of the invention, there is provided a process for preparing an N-silylorganocarbamate which comprises:

(a) providing a mixture of aminoorganosilane of the general formula:

$$R^3{}_nR^2{}_{3-n}SiR^1NH_2$$

wherein $R^1$ is a divalent hydrocarbon group of from 1 to about 20 carbon atoms; $R^2$ and $R^3$ each is independently an alkyl group containing from 1 to about 20 carbon atoms, an alkoxy group containing from 1 to about 20 carbon atoms, an aryl group containing from about 6 to about 10 carbon atoms, or an aryloxy group containing from about 6 to about 10 carbon atoms with at least one of $R^2$ and $R^3$ being a hydrolysable alkoxy group; and where n is 0 to 3, and a catalytically effective amount of basic catalyst and;

(b) combining the mixture of aminoorganosilane and basic catalyst with an organocarbonate ester of the general formula:

$$R^4OC(O)OR^4$$

wherein each $R^4$ is independently the same or different hydrocarbyl group of up to about 20 carbon atoms or halohydrocarbyl group of up to about 20 carbon atoms, or both $R^4$ groups together form a divalent alkylene group $R^5$ of from 2 to about 6 carbon atoms, the mixture of aminoorganosilane and basic catalyst, the organocarbonate ester or both being at elevated temperature at the time of their being combined, thereby producing N-silylorganocarbamate of the general formula:

$$R^3{}_nR^2{}_{3-n}SiR^1NHC(O)OR^6$$

wherein $R^1$, $R^2$ and $R^3$ have the aforestated meanings and $R^6$ is $R^4$ or $R^5H$ in which $R^4$ and $R^5$ have the aforestated meanings.

In contrast to the process described in U.S. Pat. No. 5,218,133, supra, in which aminoorganosilane is combined with a mixture of dimethyl carbonate (an organocarbonate ester) and a basic catalyst such as sodium methoxide (an alcoholate) at ambient temperature with the temperature of the reaction medium being increased only in the terminal phase of the reaction, the process of the present invention combines the organocarbonate with a mixture of aminoorganosilane and basic catalyst and does so with either the organocarbonate, the mixture of aminoorganosilane and basic catalyst or both being at elevated temperature at the time they are combined. As a result of this order of addition of the components of the reaction medium and the initially elevated temperature of at least the organocarbonate reactant or the mixture of the aminoorganosilane and basic catalyst, the process of this invention results in significantly increased production of the desired carbamate product.

DESCRIPTION OF THE PREFERRED EMBODIMENTS

In the process of this invention, aminoorganosilane and organocarbonate ester can be considered to react to form N-silylorganocarbamate in accordance with the reaction:

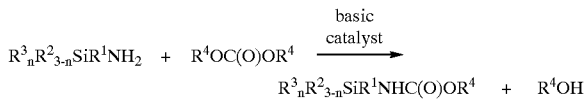

$$R^3{}_nR^2{}_{3-n}SiR^1NH_2 + R^4OC(O)OR^4 \xrightarrow{\text{basic catalyst}} R^3{}_nR^2{}_{3-n}SiR^1NHC(O)OR^4 + R^4OH$$

It will be understood that when, in organocarbonate ester $R^4OC(O)OR^4$, each $R^4$ is a different group, the reaction herein will produce a mixture of N-silylorganocarbamate products.

The aminoorganosilane used in the preparation of the N-silylorganocarbamate product of this invention is at least one compound of the general formula $R^3{}_nR^2{}_{3-n}SiR^1NH_2$ wherein $R^1$, $R^2$, $R^3$ and n have the aforestated meanings. Useful aminoorganosilane reactants include, for example, 3-aminopropyltrimethoxysilane, 3-aminopropyldimethylmethoxysilane, 3-aminopropylmethyldimethoxysilane, 3-(aminopropyl)ethyldimethoxysilane, 3-aminopropyltriethoxysilane, 3-aminopropyldimethylethoxysilane, 3-aminopropylphenyldimethoxysilane, 2-aminoethyltriethoxysilane, 4-aminobutyltriethoxysilane, 4-aminobutyltrimethoxysilane, 4-aminobutylmethyldimethoxysilane, 4-(trimethoxysilyl)-2-butanamine, 3-[diethoxy(hexyloxy)silyl]-1-propanamine, 3-[tris(pentyloxy)silyl]-1-propanamine, 3-[tris(2,2,2-trifluoroethoxy)silyl]-1-propanamine, 3-[tris[2-(2-phenoxyethoxy)ethoxy]silyl]-1-propanamine, 3-[tris[(2-ethylhexyl)oxy]silyl]-1-propanamine, 3-[tris(hexyloxy)silyl]-1-propanamine, 3-triisopropoxysilylpropylamine, 3-[tris(3-methylbutoxy)silyl]-1-propanamine, 3-[tris(2-ethoxyethoxy)silyl]-1-propanamine, 3-[bis(1,1-dimethylethoxy)methoxysilyl]-1-propanamine, 3-[(1,1-dimethylethoxy)diethoxysilyl]-1-propanamine, 3-[(1,1-dimethylethoxy)dimethoxysilyl]-1-propanamine, 3-(trimethoxysilyl)-1-pentanamine, 10,10-bis[2-(2-ethoxyethoxy)ethoxy]-3,6,9-trioxa-10-silatridecan-13-amine, and 13,13-bis[2-[2-(2-ethoxyethoxy)ethoxy]ethoxy]-3,6,9,12-tetraoxa-13-silahexadecan-16-amine, 4-amino-3,3-dimethylbutyltrimethoxysilane, 4-amino-3,3-dimethylbutyltriethoxysilane, and the like.

The aminoorganosilane can be made by any commercially available method, and preferably by the processes of copending U.S. patent application Ser. No. 60/428,323 filed Nov. 21, 2002, or U.S. Pat. No. 6,242,627 the contents of which are both hereby incorporated by reference.

The catalyst employed herein is a strong base. Preferably, the strong base is an alkoxide (alcoholate) of an alkali metal or alkaline earth metal. Examples of useful alkoxides include sodium methoxide, sodium ethoxide, calcium methoxide, calcium ethoxide, sodium propoxide, sodium tert-butoxide, potassium propoxide, potassium tert-butoxide, lithium methoxide, lithium ethoxide, lithium propoxide, lithium tert-butoxide and the like.

In general, the amount of basic catalyst employed in the process of this invention can range from about 0.01 parts by weight to 2 parts by weight per 100 parts by weight of the aminoorganosilane and organocarbonate ester. Preferably, the amount of basic catalyst ranges from about 0.2 to 0.6 parts by weight per 100 parts by weight of the aminoorganosilane and organocarbonate ester.

The aforementioned combination of aminoorganosilane and basic catalyst is combined with at least one organocarbonate ester of the general formula $R^4OC(O)OR^4$ wherein each $R^4$ has the aforestated meaning. Useful organocarbonate esters include, for example, dipropyl carbonate, diisopropyl carbonate, dibutyl carbonate, dihexyl carbonate, methyl ethyl carbonate, methyl butyl carbonate, diphenyl carbonate, methyl phenyl carbonate, ethylene carbonate, propylene carbonate, and the like and mixtures thereof.

The reaction of the aminoorganosilane with the organocarbonate ester can be carried out using stoichiometric amounts of these reactants. However, preferably, an excess of the organocarbonate ester, e.g., from about 0.05 to about 1 mole of organocarbonate ester, per mole of aminoorganosilane can be employed in the reaction. Most preferably, from about 0.1 to about 0.4 moles of excess organocarbonate ester per mole of aminoorganosilane is employed.

A principal advantage of the process of the present invention, namely, increased production of carbamate, depends upon the manner of addition of the components of the reaction medium and their temperature at the time of their combination. Specifically, the aminoorganosilane must first be mixed together with the basic catalyst prior to the resulting mixture being combined with the organocarbonate ester reactant. The requirements of the step of combining the mixture of aminoorganosilane and basic catalyst and the organocarbonate ester are satisfied by (1) combining the mixture of aminoorganosilane with an basic catalyst at elevated temperature with the organocarbonate ester at ambient temperature, or (2) combining the mixture of aminoorganosilane and basic catalyst at ambient temperature with the organocarbonate ester at elevated temperature, or (3) combining the mixture of aminoorganosilane and basic catalyst at elevated temperature with the organocarbonate ester at elevated temperature.

The advantages of the process of this invention lie not only in the increased production of carbamate but also in the significant reduction in byproducts which are commercially termed "heavies". The reaction from the start is carried out at elevated temperature thus substantially accelerating the reaction and increasing the yield of the desired N-silylorganocarbamate product.

As indicated above, the process herein is carried out with the mixture of aminoorganosilane and basic catalyst, the organocarbonate ester or both being at elevated temperature, preferably from about 50° to about 150° C. and more preferably from about 70° to about 110° C., at the time of their combination. The process can be carried out at ambient, sub-atmospheric or super-atmospheric pressure.

The process can be carried out in either a batch or continuous-feeding process of adding either the aforementioned mixture of aminoorganosilane and basic catalyst to the organocarbonate ester all at once or through a gradual feeding of the organocarbonate ester that can last from about 5 minutes to up to about 4 hours, wherein preferably, the continuous feeding is accompanied by the recycling of excess organocarbonate ester.

Upon completion of the reaction, the solution of product organocarbamate, the catalyst, the byproduct alcohol, and excess organocarbonate ester is neutralized with an acidic agent to significantly reduce the basicity and can even result in creating an acidic solution. The preferable acidic agent can be any Lewis acid but more preferably includes inorganic acids such as anhydrous phosphoric acids and most preferably organic acids such as glacial acetic acid, propionic acid, butyric acid, hexanoic acid, oleic acid, maleic acid, fumaric acid, succinic acid and the like and combinations thereof. The absence of water in the inventive process is desirous to avoid unwanted reactions and byproducts.

The aforementioned product solution can be additionally filtered and/or stripped using any known commercially available means such as vacuum or pressure filtration to remove the byproducts or volatile heavies. This filtration and/or stripping can occur either simultaneously with the neutralization or immediately thereafter.

In the product N-silylorganocarbamate $R^3{}_nR^2{}_{3-n}SiR^1NHC(O)OR^6$, $R^1$ is preferably a divalent group of an alkane, cycloalkane, aromatic or aralkane compound, for example, the same or different linear or branched alkylene group such as methylene, ethylene, 1,2-propylene, 1,3-propylene, 2-methyl-1,3-propylene, 3-methyl-1,3-propylene, 3,3-dimethyl-1,3-propylene, ethylidene, isopropylidene, 3-methyl-1,4-butylene, 3,3-dimethyl-1,4-butylene, and the like; the $R^2$ and $R^3$ groups are preferably independently selected to be alkyl, aryl, acetoxy or alkoxy groups of up to about 20 carbon atoms with at least one of $R^2$ and $R^3$ being an alkoxy group; $R^6$ is preferably the group $R^4$, the latter preferably being a lower alkyl, lower haloalkyl or aryl group, or the group —$R^5H$ with $R^5$ being ethylene (—$CH_2CH_2$—). More preferably, the $R^2$ and $R^3$ groups can be, for example, methyl, ethyl, propyl, isopropyl, butyl, tert-butyl, isobutyl, pentyl, dodecyl, methoxy, ethoxy, propoxy, isopropoxy, butoxy, phenyl or phenoxy. The $R^2$ and $R^3$ groups are most preferably selected from the group consisting of methyl, methoxy, ethyl, and ethoxy, and the like, and mixtures thereof. Whatever the nature of the $R^2$ and $R^3$ groups, at least one of these groups must be an alkoxy group, for example, any of the aforerecited alkoxy groups.

Specific N-silylorganocarbamates that can be prepared in accordance with this invention include N-(3-trimethoxysilylpropyl)methylcarbamate; [3-(triethoxysilyl) propyl]-carbamic acid nonadecyl ester; [3-(triethoxysilyl) propyl]-carbamic acid 2-[2-(2-methoxyethoxy)ethoxy]ethyl ester; carbonic acid 1,1-dimethylethyl 3-[[[[3-(triethoxysilyl)propyl]amino]carbonyl]oxy] phenyl ester; [3-(triethoxysilyl)propyl]-carbamic acid 3-phenyl-2-propenyl ester; [3-(triethoxysilyl)propyl]-carbamic acid 3,3-diphenyl-3H-naphtho[2,1-b]pyran-9-yl ester; [3-(ethoxydimethoxysilyl)propyl]-carbamic acid methyl ester; [3-(diethoxymethoxysilyl) propyl]-carbamic acid methyl ester; [3-(triethoxysilyl)propyl]-carbamic acid 3,3,4,4,5,5,6,6,7,7,8,8,8-tridecafluorooctyl ester; [3-(triethoxysilyl) propyl]-carbamic acid 1,3,5-benzenetriyltris(methylene) ester; [3-(triethoxysilyl)propyl]-carbamic acid 1,3,5-benzenetriyltris(methylene) ester; [3-(triethoxysilyl) propyl]-carbamic acid phenylmethyl ester; [3-(trimethoxysilyl)propyl]-carbamic acid ethyl ester; [3-(trimethoxysilyl)propyl]-carbamic acid 1,1-dimethylethyl ester; [3-(triethoxysilyl) propyl]-carbamic acid 1,1-dimethylethyl ester; [3-(trimethoxysilyl)propyl]-carbamic acid methyl ester; or, [3-(triethoxysilyl)propyl]-carbamic acid ethyl ester.

The entire process or any individual step therein can be done in the presence of a dry inert gas. Such gases can include nitrogen and argon and the like or mixtures thereof.

The following examples and comparative examples are illustrative of the invention.

The abbreviations used in the following examples have the following definitions

DMC=Dimethyl carbonate;

ICS=3-Isocyanatopropyltrimethoxysilane;

A-1110=3-aminopropyltrimethoxysilane;

Carbamate=N-(3-trimethoxysilylpropyl) methylcarbamate

Unel Hvs=uneluted heavies

EXAMPLE 1

In a 500 ml round-bottomed flask equipped with a pressure equalizing dropping funnel, a column with a reflux condenser, a nitrogen inlet, and a magnetic stirrer, 140 grams (0.78 mol) of A-1110 Silane were combined with 2.6 grams of a 25 wt % solution of sodium methoxide in methanol and heated to 100° C. To this stirred solution, 87.8 grams (0.97 mol) of dimethyl carbonate was added slowly over a 30-minute period to maintain the temperature to 100°±10° C. The solution was allowed to stir for a total of two hours at 100° C. before being neutralized with acetic acid and removal of the volatiles under vacuum. The contents of the reactor were sampled and analyzed by gas chromatography.

| Methanol | DMC | A-1110 | ICS | Carbamate | Uneluted Heavies |
|---|---|---|---|---|---|
| 0.9 | 0.13 | 0.19 | 0.61 | 78.85 | 17.3 |

EXAMPLE 2

In a 500 ml round-bottomed flask equipped with a pressure equalizing dropping funnel, a column with a reflux condenser, a nitrogen inlet, and a magnetic stirrer, 140 grams (0.78 mol) of A-1110 Silane were combined with 2.6 grams of a 25 wt % solution of sodium methoxide in methanol and heated to 100° C. To this stirred solution, 87.8 grams (0.97 mol) of dimethyl carbonate was added slowly over a 30-minute period to maintain the temperature to 100°±5° C. The solution was allowed to stir for a total of two hours at 83° C. before being neutralized with acetic acid and removal of the volatiles under vacuum. The contents of the reactor were sampled and analyzed by gas chromatography.

| Methanol | DMC | A-1110 | ICS | Carbamate | Uneluted Heavies |
|---|---|---|---|---|---|
| 0.36 | 0.34 | 0.19 | 0.16 | 81.3 | 14.7 |

EXAMPLE 3

In a 500 ml round-bottomed flask equipped with a pressure equalizing dropping funnel, a column with a reflux condenser, a nitrogen inlet, and a magnetic stirrer, 87.8 grams (0.97 mol) of dimethyl carbonate was warmed to 80° C. To this stirred solution was added a solution of 140 grams (0.78 mol) of A-1110 Silane and 2.6 grams of a 25 wt % solution of sodium methoxide in methanol slowly over a 30-minute period in order to maintain the temperature below 100° C. The resulting solution was allowed to stir for a total of eighty-three minutes at 80° C. before removal of the volatiles with a nitrogen sparge. The contents of the reactor were sampled and analyzed by gas chromatography.

| Methanol | DMC | A-1110 | ICS | Carbamate | Uneluted Heavies |
|---|---|---|---|---|---|
| 1.02 | 0.85 | 0.06 | 0.03 | 91.33 | 5.6 |

EXAMPLE 4

In a 500 ml round-bottomed flask equipped with a pressure equalizing dropping funnel, a column with a reflux condenser, a nitrogen inlet, and a magnetic stirrer, 140 grams (0.78 mol) of A-1110 Silane were combined with 2.6 grams of a 25 wt % solution of potassium methoxide in methanol and heated to 80° C. To this stirred solution, 87.8 grams (0.97 mol) of dimethyl carbonate was added slowly over a 30-minute period to maintain temperature to 80°±10° C. The solution was allowed to stir for one hour at 80° C. and then heated to 100° C. for one hour before being neutralized with acetic acid and removal of the volatiles with a nitrogen sparge. The contents of the reactor were sampled and analyzed by gas chromatography.

| Methanol | DMC | A-1110 | Carbamate | Uneluted Heavies |
|---|---|---|---|---|
| 15.4 | 0.15 | 5.99 | 19.13 | 24.64 |

EXAMPLE 5

In a 500 ml round-bottomed flask equipped with a pressure equalizing dropping funnel, a column with a reflux condenser, a nitrogen inlet, and a magnetic stirrer, 140 grams (0.78 mol) of A-1110 Silane were combined with 2.6 grams of a 1 molar solution of lithium methoxide in methanol and heated to 80° C. To this stirred solution 87.8 grams (0.97 mol) of dimethyl carbonate was added slowly over a 30-minute period to maintain the temperature to 80°±10° C. The solution was allowed to stir for one hour at 80° C. and then heated to 100° C. for one hour before being neutralized with acetic acid and removal of the volatiles with a nitrogen sparge. The contents of the reactor were sampled and analyzed by gas chromatography.

| Methanol | DMC | A-1110 | Carbamate | Uneluted Heavies |
|---|---|---|---|---|
| 2.34 | 0.34 | 33.26 | 27.69 | 34.22 |

EXAMPLE 6

In a 110-gallon stainless steel reactor, 141 lbs (710 mol) of dimethyl carbonate was heated to 80° C. with agitation. Over a period of approximately 35 minutes, a solution of 225 lbs (570 mol) of gamma-aminopropyltrimethoxysilane and 4 lbs of a 25 wt % solution of sodium methylate in methanol was added. After addition, the mixture was agitated at 80° C. for a total of 2 hours. The resulting solution was then cooled, neutralized with glacial acetic acid and stripped of volatile organic components. After filtering, the isolated mass of the crude carbamate, 272 lbs, was analyzed by gas chromatography.

| Methanol | DMC | A-1110 | Carbamate | Uneluted Heavies |
|---|---|---|---|---|
| 0.42 | 1.89 | nd | 90.76 | 5.91 |

EXAMPLE 7

In a 110-gallon stainless steel reactor, 265 lbs (1,018 mol) of diethyl carbonate was heated to 80° C. with agitation. Over a period of approximately 45 minutes, a solution of 438 lbs (899 mol) of gamma-aminopropyltriethoxysilane, A-1100 Silane, and 7 lbs of a 25 wt % solution of sodium ethylate in ethanol was added. After addition, the mixture was agitated at 80° C. for a total of 2.5 hours. The resulting solution was then cooled, neutralized with glacial acetic acid and stripped of volatile organic components. After filtering, the isolated mass of the crude carbamate, 500 lbs, was analyzed by gas chromatography. In this example, the carbamate is understood to be N-(3-triethoxysilylpropyl)ethyl carbamate

| Ethanol | DEC | A-1110 | Carbamate | Uneluted Heavies |
|---|---|---|---|---|
| 0.22 | 0.53 | nd | 91.56 | 5.51 |

COMPARATIVE EXAMPLE 1

In a 500 ml round-bottomed flask equipped with a pressure equalizing dropping funnel, a column with a reflux condenser, a nitrogen inlet, and a magnetic stirrer, 140 grams (0.78 mol) of A-1110 Silane was added and heated to 100° C. In a pressure equalizing dropping funnel 2.6 grams of a 25 wt % solution of sodium methoxide in methanol was combined with 87.8 grams (0.97 mol) of dimethyl carbonate and added slowly over a 30-minute period to maintain the temperature to 100°±5° C. The solution was allowed to stir for a total of two hours at 100° C. before being neutralized with acetic acid and removal of the volatiles under vacuum. The contents of the reactor were sampled and analyzed by gas chromatography.

| Methanol | DMC | A-1110 | ICS | Carbamate | Uneluted Heavies |
|---|---|---|---|---|---|
| 0.31 | 0.35 | 0.107 | 1.18 | 60.35 | 30.08 |

COMPARATIVE EXAMPLE 2

In a 500 ml round bottomed flask equipped with a pressure equalizing dropping funnel, a column with a reflux condenser, a nitrogen inlet, and a magnetic stirrer, 140 grams (0.78 mol) of A-1110 Silane was added and heated to 100° C. In a pressure equalized dropping funnel, 2.6 grams of a 25 wt % solution of sodium methoxide in methanol was combined with 87.8 grams (0.97 mol) of dimethyl carbonate and slowly added to the stirred A-1110 solution over a 30 minute period to maintain the temperature to 100°±10° C. The solution was allowed to stir for a total of two hours at 83° C. before being neutralized with acetic acid and removal of the volatiles under vacuum. The contents of the reactor were sampled and analyzed by gas chromatography.

| Methanol | DMC | A-1110 | ICS | Carbamate | Uneluted Heavies |
|---|---|---|---|---|---|
| 0.7 | 0.3 | 0.14 | 0.06 | 85.88 | 10.7 |

COMPARATIVE EXAMPLE 3

In a 500 ml round-bottomed flask equipped with a pressure equalizing dropping funnel, a column with a reflux condenser, a nitrogen inlet, and a magnetic stirrer, 2.6 grams of a 25 wt % solution of potassium methoxide in methanol was combined with 87.8 grams (0.97 mol) of dimethyl carbonate and warmed to 80° C. In a pressure equalized dropping funnel, 140 grams (0.78 mol) of A-1110 Silane was added slowly to the stirred DMC solution over a 30-minute period to maintain the temperature to 80°±2° C. The solution was allowed to stir for one hour at 80° C. and then heated to 100° C. for one hour before being neutralized with acetic acid and removal of the volatiles with a nitrogen sparge. The contents of the reactor were sampled and analyzed by gas chromatography.

| Methanol | DMC | A-1110 | Carbamate | Uneluted Heavies |
|---|---|---|---|---|
| 8.23 | 14.06 | 25.75 | 11.98 | 27.3 |

COMPARATIVE EXAMPLE 4

In a 500 ml round-bottomed flask equipped with a pressure equalizing dropping funnel, a column with a reflux condenser, a nitrogen inlet, and a magnetic stirrer, 140 grams (0.78 mol) of A-1110 Silane was heated to 80° C. To this stirred solution, a solution of 87.8 grams (0.97 mol) of dimethyl carbonate with 2.6 grams of a 1 molar solution of lithium methoxide in methanol and added slowly from a pressure equalized dropping funnel over a 30-minute period to maintain the temperature to 80°±10° C. The solution was allowed to stir for one hour at 80° C. and then heated to 100° C. for one hour before being neutralized with acetic acid and removal of the volatiles with a nitrogen sparge. The contents of the reactor were sampled periodically and analyzed by gas chromatography.

| Methanol | DMC | A-1110 | Carbamate | Uneluted Heavies |
|---|---|---|---|---|
| 2.08 | 16.32 | 25.79 | 34.34 | 19.61 |

As the data in the foregoing examples show, the process of this invention (Examples 1–7) resulted in significantly greater production of carbamate product for each catalyst tested than the prior art process (Comparative Examples 1–4).

What is claimed is:

1. A process for preparing an N-silylorganocarbamate which comprises:
   (a) providing a mixture of aminoorganosilane of the general formula:

$$R^3{}_nR^2{}_{3-n}SiR^1NH_2$$

wherein $R^1$ is a divalent hydrocarbon group of from 1 to about 20 carbon atoms; $R^2$ and $R^3$ each is independently an alkyl group containing from 1 to about 20 carbon atoms, an alkoxy group containing from 1 to about 20 carbon atoms, an aryl group containing from about 6 to about 10 carbon atoms, an aryloxy group containing from about 5 to about 10 carbon atoms or a hydrogen atom with at least one of $R^2$ and $R^3$ being an alkoxy group; and n is 0 to 3, and a catalytically effective amount of basic catalyst, and;
   (b) combining the mixture of aminoorganosilane and basic catalyst with an organocarbonate ester of the general formula:

$$R^4OC(O)OR^4$$

wherein each $R^4$ is independently the same or different hydrocarbyl group of up to about 20 carbon atoms or halohydrocarbyl group of up to about 20 carbon atoms, or each $R^4$ together forms a divalent alkylene group $R^5$ of from 2 to about 6 carbon atoms, the mixture of aminoorganosilane and alcoholate, the organocarbonate ester or both being at elevated temperature at the time of their being combined, thereby producing N-silylorganocarbamate of the general formula:

$$R^3{}_nR^2{}_{3-n}SiR^1NHC(O)OR^6$$

wherein $R^1$, $R^2$ and $R^3$ have the aforestated meanings and $R^6$ is $R^4$ or $R^5H$ in which $R^4$ and $R^5$ have the aforestated meanings.

2. The process of claim 1, wherein the $R^1$ group is methylene, ethylene, 1,2-propylene, 1,3-propylene, 2-methyl-1,3-propylene, 3-methyl-1,3-propylene, 3,3-dimethyl-1,3-propylene, ethylidene, isopropylidene, 3-methyl-1,4-butylene, or 3,3-dimethyl-1,4-butylene.

3. The process of claim 1, wherein $R^2$ and $R^3$ is each independently methyl, ethyl, propyl, isopropyl, butyl, tert-butyl, isobutyl, pentyl, dodecyl, methoxy, ethoxy, propoxy, isopropoxy, butoxy, phenyl or phenoxy.

4. The process of claim 1, wherein each $R^4$ is independently methyl, ethyl, propyl, isopropyl, butyl, hexyl or phenyl.

5. The process of claim 1, wherein $R^5$ is ethylene.

6. The process of claim 1, wherein the aminoorganosilane is 3-aminopropyltrimethoxysilane, 3-aminopropyldimethylmethoxysilane, 3-aminopropylmethyldimethoxysilane, 3-(aminopropyl)ethyldimethoxysilane, 3-aminopropyltriethoxysilane, 3-aminopropyldimethylethoxysilane, 3-aminopropylphenyldimethoxysilane, 2-aminoethyltriethoxysilane, 4-aminobutyltriethoxysilane, 4-aminobutyldimethoxysilane, 4-aminobutylmethyldimethoxysilane, 4-(trimethoxysilyl)-2-butanamine, 3-[diethoxy(hexyloxy)silyl]-1-propanamine, 3-[tris(pentyloxy)silyl]-1-propanamine, 3-[tris(2,2,2-trifluoroethoxy)silyl]-1-propanamine, 3-[tris[2-(2-phenoxyethoxy)ethoxy]silyl]-1-propanamine, 3-[tris[(2-ethylhexyl)oxy]silyl]-1-propanamine, 3-[tris(hexyloxy)silyl]-1-propanamine, 3-triisopropoxysilylpropylamine, 3-[tris(3-methylbutoxy)silyl]-1-propanamine, 3-[tris(2-ethoxyethoxy)silyl]-1-propanamine, 3-[bis(1,1-dimethylethoxy)methoxysilyl]-1-propanamine, 3-[(1,1-dimethylethoxy)diethoxysilyl]-1-propanamine, 3-[(1,1-dimethylethoxy)dimethoxysilyl]-1-propanamine, 3-(trimethoxysilyl)-1-pentanamine, 10,10-bis[2-(2-ethoxyethoxy)ethoxy]-3,6,9-trioxa-10-silatridecan-13-amine, and 13,13-bis[2-[2-(2-ethoxyethoxy)ethoxy]ethoxy]-3,6,9,12-tetraoxa-13-silahexadecan-16-amine, 4-amino-3,3-dimethylbutyltrimethoxysilane or 4-amino-3,3-dimethylbutyltriethoxysilane.

7. The process of claim 1, wherein the organocarbonate ester is dimethyl carbonate, diethyl carbonate, dipropyl carbonate, diisopropyl carbonate, dibutyl carbonate, dihexyl carbonate, methyl ethyl carbonate, methyl butyl carbonate, diphenyl carbonate or methyl phenyl carbonate, ethylene carbonate or propylene carbonate.

8. The process of claim 1, wherein the basic catalyst is an alkoxide of an alkali metal or alkaline earth metal.

9. The process of claim 8, wherein the alkoxide is sodium methoxide, sodium ethoxide, sodium propoxide, sodium tert-butoxide, potassium methoxide, potassium ethoxide, potassium propoxide, potassium tert-butoxide, lithium methoxide, lithium ethoxide, lithium propoxide or lithium tert-butoxide.

10. The process of claim 1, wherein the aminoorganosilane is 3-aminopropyltrimethoxysilane, 3-aminopropyldimethylmethoxysilane, 3-aminopropylmethyldimethoxysilane, 3-(aminopropyl)ethyldimethoxysilane, 3-aminopropyltriethoxysilane, 3-aminopropyldimethylethoxysilane, 3-aminopropylphenyldimethoxysilane, 2-amino ethyltriethoxysilane, 4-aminobutyltriethoxysilane, 4-aminobutyldimethoxysilane, 4-aminobutylmethyldimethoxysilane, 4-(trimethoxysilyl)-2-butanamine, 3-[diethoxy(hexyloxy)silyl]-1-propanamine, 3-[tris(pentyloxy)silyl]-1-propanamine, 3-[tris(2,2,2-trifluoroethoxy)silyl]-1-propanamine, 3-[tris[2-(2-phenoxyethoxy)ethoxy]silyl]-1-propanamine, 3-[tris[(2-ethylhexyl)oxy]silyl]-1-propanamine, 3-[tris(hexyloxy)silyl]-1-propanamine, 3-triisopropoxysilylpropylamine, 3-[tris(3-methylbutoxy)silyl]-1-propanamine, 3-[tris(2-ethoxyethoxy)silyl]-1-propanamine, 3-[bis(1,1-dimethylethoxy)methoxysilyl]-1-propanamine, 3-[(1,1-dimethylethoxy)diethoxysilyl]-1-propanamine, 3-[(1,1-dimethylethoxy)dimethoxysilyl]-1-propanamine, 3-(trimethoxysilyl)-1-pentanamine, 10,10-bis[2-(2-ethoxyethoxy)ethoxy]-3,6,9-trioxa-10-silatridecan-13-amine, and 13,13-bis[2-[2-(2-ethoxyethoxy)ethoxy]ethoxy]-3,6,9,12-tetraoxa-13-silahexadecan-16-amine, 4-amino-3,3-dimethylbutyltrimethoxysilane, 4-amino-3,3-dimethylbutyltriethoxysi lane, the organocarbonate ester is dimethyl carbonate, diethyl carbonate, dipropyl carbonate, diisopropyl carbonate, dibutyl carbonate, dihexyl carbonate, methyl ethyl carbonate, methyl butyl carbonate, diphenyl carbonate methyl phenyl carbonate, ethylene carbonate or propylene carbonate and the basic catalyst is sodium methoxide, sodium ethoxide, sodium propoxide, sodium tert-butoxide, potassium methoxide, potassium ethoxide, potassium propoxide, potassium tert-butoxide, lithium methoxide, lithium ethoxide, lithium propoxide or lithium tert-butoxide.

11. The process of claim 1, wherein the prepared N-silylorganocarbamate is [3-(triethoxysilyl)propyl]-carbamic acid nonadecyl ester; [3-(triethoxysilyl)propyl]-carbamic acid 2-[2-(2-methoxyethoxy)ethoxy]ethyl ester; carbonic acid 1,1-dimethylethyl 3-[[[[3-(triethoxysilyl)propyl]amino]carbonyl]oxy]phenyl ester; [3-(triethoxysilyl)propyl]-carbamic acid 3-phenyl-2-propenyl ester; [3-(triethoxysilyl)propyl]-carbamic acid 3,3-diphenyl-3H-naphtho[2,1-b]pyran-9-yl ester; [3-(ethoxydimethoxysilyl)propyl]-carbamic acid methyl ester; [3-(diethoxymethoxysilyl) propyl]-carbamic acid methyl ester; [3-(triethoxysilyl)propyl]-carbamic acid 3,3,4,4,5,5,6,6,7,7,8,8,8-tridecafluorooctyl ester; [3-(triethoxysilyl)propyl]-carbamic acid 1,3,5-benzenetriyltris(methylene) ester; [3-(triethoxysilyl)propyl]-carbamic acid phenylmethyl ester; [3-(trimethoxysilyl)propyl]-carbamic acid ethyl ester; [3-(trimethoxysilyl)propyl]-carbamic acid 1,1-dimethylethyl ester; [3-(triethoxysilyl) propyl]-carbamic acid 1,1-dimethylethyl ester; [3-(trimethoxysilyl)propyl]-carbamic acid methyl ester; or, [3-(triethoxysilyl)propyl]-carbamic acid ethyl ester.

12. The process of claim 1, wherein the organocarbonate ester is present in stoichiometric excess.

13. The process of claim 12, wherein the process is a continuous process and excess organocarbonate ester is recycled.

14. The process of claim 1, wherein the elevated temperature is from about 50° to about 150° C.

15. The process of claim 1, wherein the elevated temperature is from about 70° to about 110° C.

16. The process of claim 1, wherein the product N-silylorganocarbamate is neutralized with an acidic agent.

17. The process of claim 16, wherein the acidic agent is anhydrous hydrochloric acid, anhydrous phosphoric acids, glacial acetic acid, propionic acid, butyric acid, hexanoic acid, oleic acid, maleic acid, fumaric acid, succinic acid or mixtures thereof.

18. The process of claim 16, wherein the neutralized N-silylorganocarbamate is filtered using pressure and/or vacuum filtration to remove volatiles.

19. The process of claim 18, wherein the filtration is conducted in the presence of a dry inert gas.

20. The process of claim 18, wherein the N-silylorganocarbamate is stripped to remove any excess alcohol or byproduct.

* * * * *